(12) United States Patent
Korkor

(10) Patent No.: US 6,722,705 B2
(45) Date of Patent: Apr. 20, 2004

(54) MEDICAL TUBING CONNECTOR

(75) Inventor: Adel B. Korkor, Hartland, WI (US)

(73) Assignee: AB Korkor Medical, Inc., Hartland, WI (US)

(*) Notice: Subject to any disclaimer, the term of this patent is extended or adjusted under 35 U.S.C. 154(b) by 0 days.

(21) Appl. No.: 10/132,849

(22) Filed: Apr. 25, 2002

(65) Prior Publication Data

US 2003/0201639 A1 Oct. 30, 2003

(51) Int. Cl.$^7$ ................................................ F16L 35/00
(52) U.S. Cl. ...................... 285/332; 285/332.1; 285/92; 285/84; 285/86; 285/148.6; 285/604; 285/533; 285/534; 285/535
(58) Field of Search ........................... 285/332, 332.1, 285/92, 84, 86, 85, 148.6, 89; 604/533, 534, 535

(56) References Cited

U.S. PATENT DOCUMENTS

| | | | | |
|---|---|---|---|---|
| 2,070,077 A | * | 2/1937 | Davis | 285/89 |
| 4,421,507 A | * | 12/1983 | Bokros | 604/52 |
| 4,432,764 A | * | 2/1984 | Lopez | 604/283 |
| 4,534,585 A | | 8/1985 | Saliger | |
| 4,895,570 A | | 1/1990 | Larkin | |
| 5,176,415 A | * | 1/1993 | Choksi | 285/331 |
| 5,391,152 A | | 2/1995 | Patterson | |
| 5,833,275 A | | 11/1998 | Andersen | |
| 5,855,568 A | * | 1/1999 | Battiato et al. | 604/240 |
| 5,928,208 A | * | 7/1999 | Chu et al. | 604/280 |
| 6,042,577 A | * | 3/2000 | Chu et al. | 604/523 |
| 6,165,149 A | * | 12/2000 | Utterberg et al. | 604/5.01 |
| 6,217,564 B1 | | 4/2001 | Peters et al. | |
| 6,290,688 B1 | | 9/2001 | Lopez et al. | |
| 6,508,807 B1 | | 1/2003 | Peters | |
| 2001/0049490 A1 | * | 12/2001 | Slanda et al. | |

FOREIGN PATENT DOCUMENTS

| | | |
|---|---|---|
| DE | 367 152 | 1/1923 |
| DE | 298 13 140 | 10/1998 |
| DE | 200 11 161 | 3/2001 |
| GB | 2 379 253 | 3/2003 |
| WO | WO 00/63604 | 10/2000 |

OTHER PUBLICATIONS

Bard Access Systems, *Catheter Repair Kit for Vas–Cath® Polyurethane Dialysis Catheters*, 2 pages (undated).

* cited by examiner

Primary Examiner—David Bagnell
Assistant Examiner—G M Collins
(74) Attorney, Agent, or Firm—Boyle Fredrickson Newholm Stein & Gratz S.C.

(57) ABSTRACT

A medical connector, usable to securely couple a first tubular medical device to a second tubular medical device, includes first and second fittings cooperating with the first and second medical devices, respectively. The first and second fittings may each include a nipple, a ferrule, or some other structure that is connected to the associated medical device and that is connectable to the other fitting. The second fitting may additionally include a tubular sleeve that slides over the second medical device and the ferrule or other component of the second fitting. The two components of the second fitting are sequentially connectable to the first fitting through distinctly different motions to provide a redundant, secure connection. For example, the first fitting may include a first set of left-handed threads and a second set of right-handed threads, and the components of the second fitting may have corresponding left-handed and right-handed threads.

13 Claims, 2 Drawing Sheets

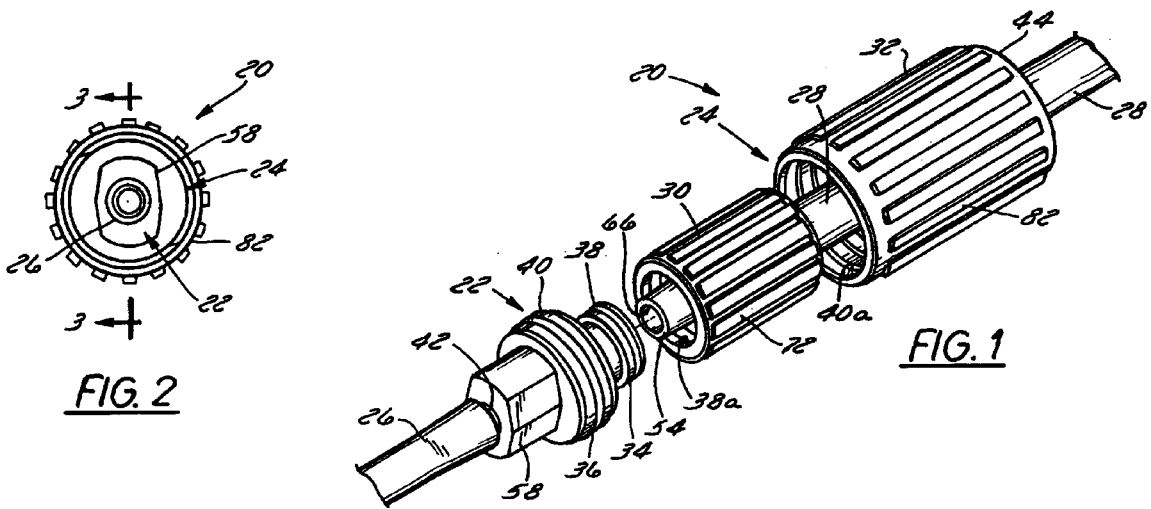
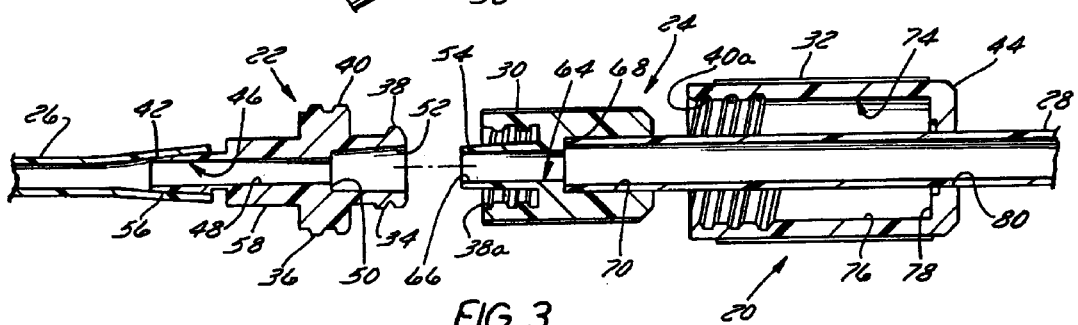

MEDICAL TUBING CONNECTOR

FIELD OF THE INVENTION

The invention relates to medical devices, and, in particular, to connectors for tubular medical devices such as catheters and needles.

DESCRIPTION OF THE RELATED ART

Catheters are flexible tubes used for withdrawing fluids from or injecting fluids into a patient's body. Catheters can be used to introduce or withdraw fluids from, for example, a body cavity, duct, vein, or artery (hereafter referred to as "blood vessels" for the sake of simplicity). For example, catheters are inserted into a patient's gastric tube for feeding or into an ileostomy for draining fluids to a drain bag.

Some catheters can be directly inserted into a patient, e.g., with an introducer needle, which is withdrawn after insertion, leaving the catheter in the patient. Other catheters, such as a Foley catheter, which is used to drain urine from a bladder, is inserted directly into a patient without the use of a needle. Still other catheters are connected to a patient with a needle that remains in the patient.

Catheters are also used during dialysis, a process that cleanses blood. There are two types of dialysis: hemodialysis and peritoneal dialysis. During hemodialysis, blood is removed from the patient and transferred to a machine, where it is cleaned by filtration through a semi-permeable membrane. During filtration, a dialysate is located on one side of the membrane and blood is located on the other side. Waste particles pass from the blood through the membrane to the dialysate, which washes the waste particles away. Cleansed blood is then returned to the patient.

For more permanent access, before hemodialysis is performed, a doctor can surgically make an entrance into the patient's blood vessels. In many cases, a doctor surgically creates a "fistula" by joining an artery to a vein to make a larger vessel. Alternatively, a doctor can use a soft plastic tube called a vascular graft to join an artery and a vein under the skin. For more temporary access, a doctor can implant a catheter into, e.g., a large blood vessel in the patient's neck. After access is made and healed, two needles are inserted into the fistula or graft, with one implanted in a vein side and one implanted in an artery side.

In peritoneal dialysis, the patient's own peritoneal membrane is used as a semi-permeable filter. Prior to beginning peritoneal dialysis, a doctor implants a peritoneal catheter in the patient's abdomen. The patient adds a dialysate fluid through the catheter to the abdomen. As the patient's blood is exposed to the dialysate through the peritoneal membrane, impurities in the blood are drawn through the membrane walls and into the dialysate. The patient drains out the dialysate after three or more hours and pours in fresh fluid.

Peritoneal dialysis is often performed while a patient is sleeping. Where patients turn over or otherwise move during sleep, there is a risk that the peritoneal catheter can unintentionally decouple from the patient. The danger of unintentionally decoupling a catheter connection is particularly acute with patients who, e.g., are agitated or have dementia.

Many other procedures require the secure connection of the sections of tubing or other tubular medical devices such as needles. In many of these procedures, including those described above, it is important to ensure that the connector keeps the catheter connected to a second catheter or to a needle until it is desired to disconnect it. For example, accidental disconnection of a catheter can lead to many serious problems including loss of blood and contamination of the surroundings and/or medical personnel and the cessation of medication delivery. For example, during hemodialysis, if a catheter accidentally disconnects and no intervention occurs, a patient can lose a liter of blood in two minutes and bleed to death in five minutes.

Traditional medical connectors typically include either a threaded connection or a friction fit coupling to connect medical sections of tubing or other tubular medical devices such as needles. In a threaded connection, at least one part of the connector includes threads and the other part includes threads or lugs that are received in the threads. One part is turned relative to the other to make the connection. This type of medical connector is prone to unintentional decoupling. In a fraction fit coupling, a male fitting having a frustoconical shape is inserted into a female fitting having a frustoconical-shaped receiving cavity. Opposing conical surfaces on the female and male fittings come into contact with each other and form a friction fit. This type of adaptor is also susceptible to accidental disconnecting.

In view of the foregoing, it would be desirable to provide a connector that minimizes or prevents accidental disconnection of, e.g., a first piece of medical tubing, such as a catheter, from, e.g., a second piece of medical tubing or from a needle. It would also be desirable to provide a method of connecting and disconnecting medical tubing from, e.g., other pieces of medical tubing or needles such that they do not unintentionally decouple.

SUMMARY OF THE INVENTION

The invention, which is defined by the claims set out at the end of this disclosure, is intended to solve at least some of the problems noted above. To summarize, the connector includes a first fitting which is configured to be connectable to a first tubular medial device and a second fitting which is configured to be connectable to a second tubular medical device. The first and second fittings have first and second connections thereon that require the sequential performance of two distinct motions of different direction to couple the first and second fittings to one another. For example, the first and second connections may comprise threaded connections of opposite handedness.

Advantageously, the second fitting may be a multi-component fitting including a ferrule and a sleeve. The ferrule of this fitting may have an outer diameter that is smaller than an inner diameter of the sleeve such that the sleeve can slidably receive the ferrule. In this case, a female portion of the first connection is located on the ferrule, and a corresponding male portion of the first connection is located on the first fitting. Similarly, a female portion of the second connection is located on the sleeve, and a male portion of the second connection is located on the first fitting, inwardly from the male portion of the first connection.

In accordance with another aspect of the invention, a method of coupling two tubular medical devices together includes connecting a first fitting of a medical connector to a second fitting of the medical connector at a first connection in a first motion, then connecting the first fitting to the second fitting at a second connection in a second motion, wherein the first and second motions are distinct and are of different directions. Preferably, the connecting steps include turning the first and second fittings relative to each other with the first set of connections taking place when the fittings are turned in a first direction and the second set of connections taking place when the fittings are turned in a second, opposite direction.

BRIEF DESCRIPTION OF THE DRAWINGS

Preferred exemplary embodiments of the invention are illustrated in the accompanying drawings, in which like reference numerals represent like parts throughout and in which:

FIG. 1 is an exploded perspective view of a medical connector made in accordance with a preferred embodiment of the invention, showing a first tube, a second tube, and a third tube of the connector in an unassembled state, and showing the medical connector with medical tubing attached to the first and second tubes;

FIG. 2 is a top plan view of the connector of FIG. 1;

FIG. 3 is a sectional view taken along line 3—3 of FIG. 2;

Figure 4:
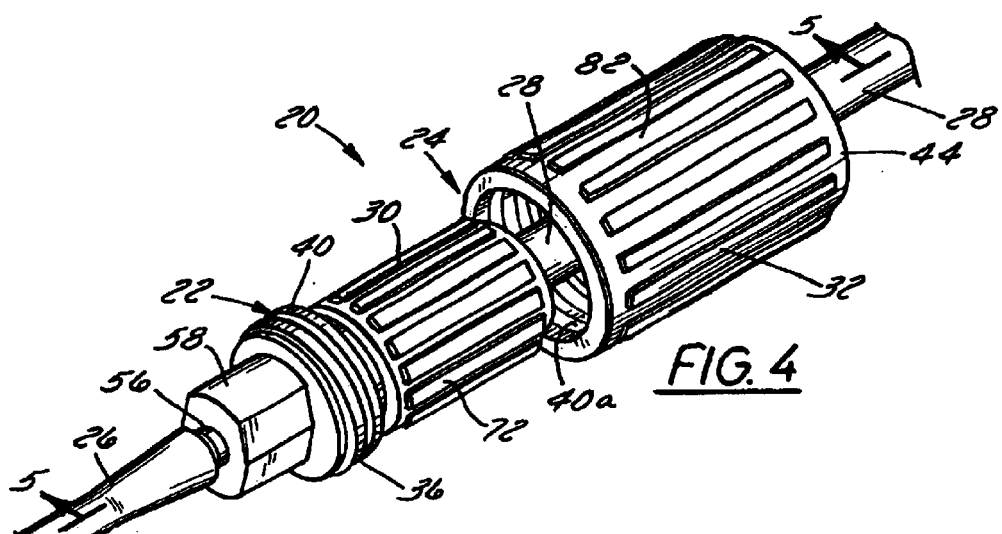
FIG. 4 is a partially exploded view of the connector of FIGS. 1–3, showing the connector partially assembled.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

1. Resume

Pursuant to the invention, a medical connector is provided that can be used to securably couple a first tubular medical device such as a first section of tubing, a catheter, or a needle to a second tubular medical device such as a second section of tubing, a catheter, or a needle. The connector includes first and second fittings cooperating with the first and second medical devices, respectively. The first and second fittings may each include a nipple, a ferrule, or some other structure that is connected to the associated medical device and that is connectable to the other fitting. The second fitting may additionally include a tubular sleeve that slides over the second medical device and the ferrule or other component of the second fitting. The two components of the second fitting are sequentially connectable to the first fitting through distinctly different motions to provide a redundant, secure connection. For example, the first fitting may include a first set of left-handed threads and a second set of right-handed threads, and the components of the second fitting may have corresponding left-handed and right-handed threads.

2. Preferred Embodiment of the Connector

A preferred embodiment of the medical connector 20 is illustrated in FIGS. 1–3. The medical connector 20 includes first and second fittings 22 and 24 associated with first and second tubular medical devices 26 and 28, respectively. In the illustrated embodiment, the first medical device 26 comprises a first section of medical tubing that directs fluid to or from a device inserted into a patient's body. For example, the first section of medical tubing 26 may lead to a needle, a catheter, or the like. The second medical device 28 of this embodiment is a second section of medical tubing that leads away from the patient to, e.g., a drain bag, an infusion bag, or a hemodialysis machine. The first fitting 22 preferably comprises a male nipple 22 mounted on the first section of tubing. The second fitting 24 is preferably a two-part female fitting 24 including 1) a ferrule 30 and 2) a sleeve 32 mounted on the second section of tubing 28. The two components of the second fitting 24 are sequentially connectable to the first fitting 22 in opposite manners to one another. In a preferred embodiment, the first fitting 22 includes first and second threaded portions 34 and 36, respectively, that have threads 38 and 40 of opposite handedness for connection to corresponding threads 38a and 40a on the ferrule 30 and the sleeve 32, respectively. All three components 22, 30, and 32 preferably are formed from a medical grade polymer, such as acyclonitrile-butadiene styrene, fluorinated ethylene-propethylene (FEP), polyethylene (PE), polypropylene, polyvinyl chloride, or the like and are preferably formed by injection molding.

In the illustrated embodiment in which the first fitting 22 is configured to be at least indirectly connected to a device to be inserted into a patient, the left-most end 42 of the connector 20 as viewed in the drawings can be considered as the proximal end of the connector 20, and the right-most end 44 can be considered the distal end. The respective components 22, 30, and 32 can likewise be considered to have corresponding proximal and distal ends. It must be emphasized, however, that relative terms like "proximal" and "distal" are used only as a frame of reference and that the orientation of the opposed ends of the connector 20 may vary, depending on the application.

The first fitting 22 comprises a stepped molded plastic nipple having a stepped bore 46 formed therethrough that extends parallel to a longitudinal axis of the distal end of the first tubing section 26. As can be seen best in FIG. 3, the bore 46 includes a first, proximal portion 48, a step 50, and a second, distal portion 52 terminating at the distal end of the first fitting 22. The first portion 48 of the bore 46 forms part of the fluid pathway of the medical connector 20. The second portion 52 has a larger diameter than the first portion 48 and is configured and dimensioned such that a cylindrical extension 54 of the ferrule 30 (detailed below) can be received therein.

At its proximate side of the outer surface, the first fitting 22 includes a connection 56 that is configured to receive the first tubing section 26 in a standard manner as shown in FIG. 1. The exterior of the first fitting 22 also includes a flat-sided portion 58 (six-sided in the illustrated embodiment) located adjacent the connection 56. The flat-sided portion 58 improves the grippability of the first fitting 22 as it is being connected to the second fitting 24 using either fingers or a wrench. The second threaded portion 36 of the first fitting 22 is a relative large diameter threaded portion that is located axially adjacent the flat-sided portion 58 for connection with the sleeve 32 of the second fitting 24. The first threaded portion 34 of the first fitting 22 is a relatively small diameter threaded portion that is located axially adjacent the large diameter threaded portion 36 at the distal end of the first fitting 22 for connection to the ferrule 30 of the second fitting 24. As discussed above, the threads 38, 38a, 40, and 40a on the first and second threaded portions 34 and 36 are of opposite handedness.

The ferrule 30 of the second fitting 24 comprises a molded plastic element having a stepped bore 64 formed therethrough that extends parallel to a longitudinal axis of the proximal end of the second tubing section 28 and to the bore 46 in the first fitting 22. As can best be seen in FIG. 3, the bore 64 includes a first portion 66, which is on the proximal end of the ferrule 30, a step 68, and a second portion 70, which is on the distal end of the ferrule 30 and which has a diameter that is larger than that of the first portion 66 and approximately the same as the outer diameter of the second tubing section 28. The first portion 66 forms part of the fluid pathway. Preferably, the second tubing section 28 or any other tubular medical device can be affixed to the second portion 70 in a friction fit or with an epoxy or a solvent, such as ethyl cyanoacrylate.

Figure 5:
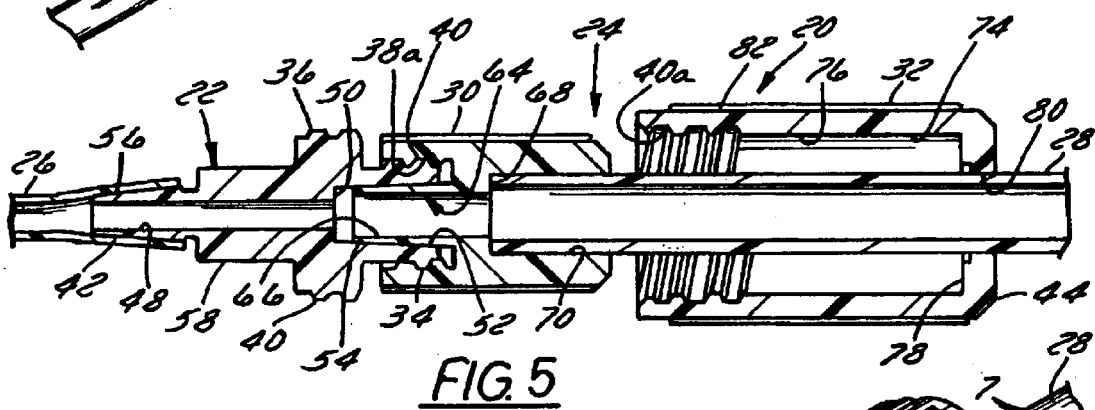
FIG. 5 is a cross sectional view taken along line 5—5 of FIG. 4.

Finally, the ferrule 30 is counterbored and internally threaded with the threads 38a at its proximal end to threadedly receive the threads 38 of the second threaded portion 36 of the first fitting 22 as seen in FIGS. 4 and 5. The cylindrical extension 54 is located on a proximal end of the ferrule 30 radially inwardly from the threads 38a and extends beyond the proximal end of the remainder of the ferrule 30. The cylindrical extension 54 has an outer diameter that is slightly smaller than the diameter of the second end 52 of the bore 46 in the first fitting 22 such that the cylindrical extension 54 can be received inside the first fitting 22. Finally, the outer surface of the ferrule 30 includes axially extending ribs 72 to enhance the graspability of the ferrule 30 as it is being secured to the first fitting 22.

Figure 6:
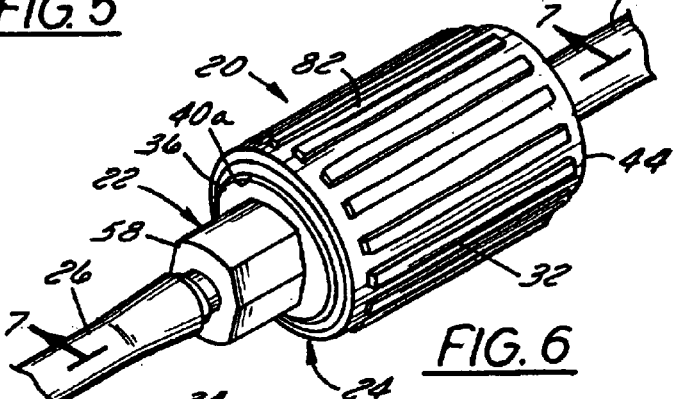
FIG. 6 is a perspective view of the connector of FIGS. 1–5, showing the connector fully assembled.
Figure 7:
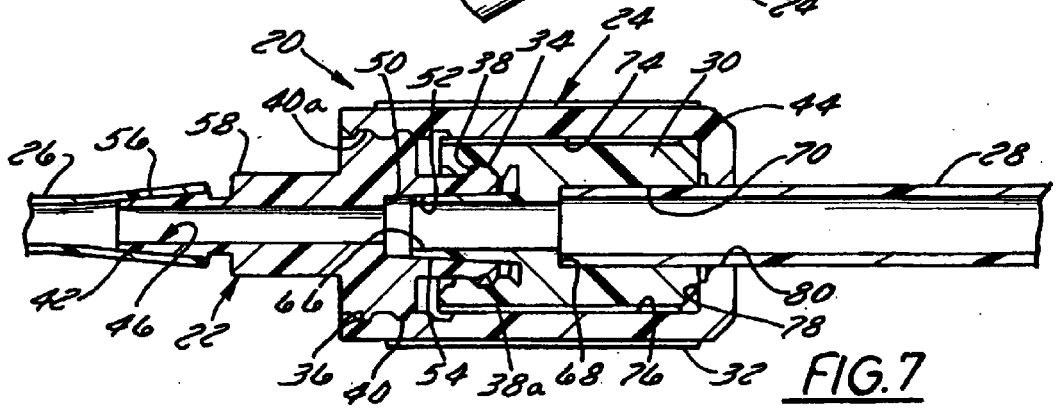
FIG. 7 is a cross sectional view taken along line 7—7 of FIG. 6.

The sleeve 32 of the second fitting 24 has an axial through-bore 74 that extends the length of the sleeve 32. As can best be seen in FIG. 3, the bore 74 includes a first portion 76 of relatively large diameter that extends most of the length of the sleeve 32 from the sleeve's proximal end, a step 78, and a second portion 80 of relatively small diameter that extends from the step 78 to the distal end of the sleeve 32. The first portion 76 is dimensioned to be slightly larger than the outer diameter of the ferrule 30 such that the ferrule 30 can fit into the sleeve 32. The first portion 76 of the bore 74 is also internally threaded with threads 40a at its outer end so as to be connectable to the threads 40 on the second threaded portion 36 of the first fitting 22 when the ferrule 30 is threaded onto the first threaded portion 34 of the first fitting 22 and the sleeve 32 is slid over the ferrule 30 as seen in FIGS. 6 and 7. The second portion 80 of the bore 74 is dimensioned to receive the second tubing section 28 in a sliding manner such that the sleeve 32 can float over the second tubing section 28. The outer surface of the sleeve 32, like the outer surface of the ferrule 30, has axially extending ribs 82 to enhance the graspability of the sleeve 32 as it is being connected to the first fitting 22.

3. Operation of the Connector

Typical use of the connector 30 of the preferred embodiment will now be described. Prior to connection, the bayonet fitting 56 on the proximal end of the first fitting 22 will be inserted into the end of the first tubing section 26, and the second fitting 24 will be mounted over the end of the second tubing section 28 as described above, with the sleeve 32 being slid onto the second tubing section 28 before the ferrule 30 is glued onto or otherwise affixed to the second tubing section 28. The parts then assume the relationships illustrated in FIGS. 1–13.

Referring now to FIGS. 4 and 5, to couple the connector 20, the distal end of the first fitting 22 is axially aligned with the proximal end of the second fitting 24. The distal, first portion 34 of the first fitting 22 is inserted into the proximal, female portion of the ferrule 30 and is connected thereto, preferably by turning the first fitting 22 relative to the ferrule 30 in a first direction to engage the threads 38 and 38a on the female and male portions of the respective components 22 and 30. The cylindrical extension 54 on the ferrule 30 extends into the distal portion 52 of the bore 46 in the first fitting 22 at this time to form a contiguous, fluid tight flow path from the first tubing section 26, through the proximal portion 48 of bore 46 in the first fitting 22, through the proximal portion 66 of the bore 64 in the ferrule 30, and into the second tubing section 28. The components 22 and 30 are fully coupled when the threads 38 and 38a bottom out or the cylindrical extension 54 of the ferrule 30 engages the step 50 in the bore 46 of the first fitting 22, whichever occurs first. The connector 22 assumes the position of FIGS. 4 and 5 at this time.

Referring now to FIGS. 6 and 7, the sleeve 32 is readied for connection with the proximate end of the first fitting 22 by sliding the sleeve 32 over the distal end of the ferrule 30 and toward the first fitting 22. The sleeve 32 slides over the ferrule 30 during the process until the internal threads 40a in the sleeve 32 meet the external threads 40 on the second, larger-diameter threaded portion 36 of the first fitting 22. The sleeve 32 is then threaded out the first fitting 22 by turning the sleeve 32 relative to the ferrule 30 and first fitting 22 in a second direction, which is opposite the first direction, to engage the second set of threads 40 and 40a. The components 22 and 32 are fully coupled when the threads 40 and 40a bottom out or the step 78 in the sleeve 32 engages the distal end of the ferrule 30, whichever occurs first.

To decouple the connector 30, the sleeve 32 is turned relative to the first fitting 22 to uncouple the sleeve 32 from the first fitting 22. If desired, the sleeve 32 can be slipped away from the first fitting 22 and the ferrule 30. Next, the first fitting 22 is released by turning the ferrule 30 relative to the first fitting 22 in a direction that is opposite the direction.

Hence, two sequential motions of distinctly different and, preferably, at least generally opposite directions are required to either couple or decouple the first and second tubing sections 26 and 28 or any other tubular medical devices. Requiring this motion greatly reduces or avoids unintentional decoupling of the connector 20. This feature is particularly useful for patients that are, e.g., agitated.

It is understood that the various preferred embodiments are shown and described above to illustrate different possible features of the invention and the varying ways in which these features may be combined. For instance the first and second fittings 22 and 24 could be connected to one another using connections other than traditional threaded connections. For example, one or both of the threaded connections could be replaced with a threaded luer lock connection. In a threaded luer lock connection, typically a male portion of the fitting has a pair of lugs that are located on opposite sides of the male portion. The lugs are configured and dimensioned to be accepted in threads or grooves in a female portion of the connector. Still other connections are possible, so long as two or more distinct actions are required to connect or disconnect the coupled devices. In addition, one or both of the fittings could also have more than two components, further enhancing the security of the connection. Other changes falling within the scope of the invention will become apparent from the appended claims.

What is claimed is:

1. A medical connector comprising:

(A) a first fitting which is configured to be connectable to a first tubular medical device; and (B) a second fitting which is configured to be connectable to a second tubular medical device, wherein the second fitting has first and second components that are individually mountable over a common end of the first fitting and that are attachable to the first fitting only through the sequential performance of at least two distinct motions of different directions, wherein the first component of the second fitting comprises a ferrule and the second component of the second fitting comprises a sleeve, and wherein the ferrule has an outer diameter that is smaller than an inner diameter of the sleeve such that the sleeve can slidably receive the ferrule.

2. A medical connector of claim 1, wherein the first fitting includes first and second threaded portions having threads of opposite first and second handedness and the first component of the second fitting has threads corresponding to the first handedness and the second component of the second fitting has threads corresponding to the second handedness.

3. A medical connector of claim 2, wherein the first handedness is one of left-handed threaded and right-handed threaded, and the second handedness is the other of left-handed threaded and right-handed threaded.

4. A medical connector of claim 1, wherein at least one of the first and second components is attachable to the first fitting via a threaded luer fitting.

5. A medical connector of claim 1, wherein an outer surface of the ferrule and the sleeve includes axially extending ribs.

6. A medical connector of claim 1, wherein the ferrule includes a female portion, and the first fitting includes a first male portion that connects to the female portion of the ferrule, and wherein the sleeve includes a female portion and the first fitting includes a second male portion inwardly from the first male portion of the first fitting, that connects to the female portion of the sleeve.

7. A medical connector of claim 1, further comprising a cylindrical extension that is located on the ferrule and that has an outer diameter that is smaller than an inner diameter of a male portion of the first fitting such that the cylindrical extension can be received inside of the first fitting.

8. A medical connector of claim 11, wherein the ferrule is configured to be affixed to the second tubular medical device.

9. A medical connector comprising:
(A) a first fitting which is configured to be connectable to a first tubular medical device; and
(B) a second fitting which is configured to be connectable to a second tubular medical device, wherein the second fitting has first and second components that are individually mountable over a common end of the first fitting and that are attachable to the first fitting only through the sequential performance of at least two distinct motions of different directions,
wherein the first component of the second fitting comprises a ferrule and the second component of the second fitting comprises a sleeve, and
wherein the sleeve is dimensioned and configured to slide over the second tubular medical device.

10. A medical connector comprising:
(A) a first fitting which is configured to be connectable to a first tubular medical device; and
(B) a second fitting which is configured to be connectable to a second tubular medical device, wherein the second fitting has first and second components that are individually mountable over a common end of the first fitting and that are attachable to the first fitting only through the sequential performance of at least two distinct motions of different directions,
wherein the first component of the second fitting comprises a ferrule and the second component of the second fitting comprises a sleeve, and
wherein the first fitting comprises:
  (A) a first fitting portion that is configured to receive the first tubular medical device;
  (B) a flat-sided portion axially adjacent the first fitting portion;
  (C) a second, threaded fitting portion axially adjacent the flat-sided portion for connection with the sleeve; and
  (D) a third, threaded fitting portion axially adjacent the second fitting portion for connection with the ferrule, wherein the second fitting portion has an outer diameter that is larger than an outer diameter of the third fitting portion.

11. A medical connector comprising:
(A) a first fitting which is configured to be connectable to a first tubular medical device; and
(B) a second fitting which is configured to be connectable to a second tubular medical device, wherein the second fitting has first and second components that are individually mountable over a common end of the first fitting and that are attachable to the first fitting only through the sequential performance of at least two distinct motions of different directions,
wherein the first component of the second fitting comprises a ferrule and the second component of the second fitting comprises a sleeve, and
wherein the ferrule comprises a stepped bore formed therethrough, the stepped bore comprising:
  (A) a first portion;
  (B) a step;
  (C) a second portion that terminates at a distal portion of the ferrule, wherein a diameter of the second portion is greater than the diameter of the first portion and is approximately the same size as an outer diameter of the second tubular device.

12. A method comprising:
(A) providing a medical connector including a first fitting that is connectable to a first fluid delivery device and a second fitting that is connectable to a second fluid delivery device;
(B) during a first motion, connecting the first fitting of the medical connector to a ferrule of a second fitting through relative movement between the ferrule and the first fitting in a first direction; then
(C) sliding a sleeve of the second fitting over the ferrule; then
(D) during a second, distinct, motion, connecting the first fitting of the medical connector to the sleeve of the second fitting through relative movement between the sleeve and the first fitting in a second, different direction.

13. A method of claim 12, wherein the first and second directions are different rotational directions of opposite handedness.

* * * * *